US008608687B2

(12) United States Patent
Patil et al.

(10) Patent No.: US 8,608,687 B2
(45) Date of Patent: Dec. 17, 2013

(54) MULTI-LUMEN ENDOSCOPIC ACCESSORY AND SYSTEM

(75) Inventors: Abhitabh Patil, Chicago, IL (US); Michael Gadaleta, New Milford, NJ (US); Karan Raturi, Duluth, GA (US); Ashish Patil, Lansdale, PA (US); Nikhil Dewan, Reston, VA (US)

(73) Assignee: Medivity, LLC, Suwanee, GA (US)

( * ) Notice: Subject to any disclaimer, the term of this patent is extended or adjusted under 35 U.S.C. 154(b) by 476 days.

(21) Appl. No.: 12/848,545

(22) Filed: Aug. 2, 2010

(65) Prior Publication Data
US 2011/0028783 A1    Feb. 3, 2011

Related U.S. Application Data

(60) Provisional application No. 61/230,175, filed on Jul. 31, 2009.

(51) Int. Cl.
*A61M 31/00*    (2006.01)
*A61M 37/00*    (2006.01)

(52) U.S. Cl.
USPC .................. 604/95.03; 604/264; 604/540

(58) Field of Classification Search
USPC ................... 604/264, 272, 529, 533–535
See application file for complete search history.

(56) References Cited

U.S. PATENT DOCUMENTS

2009/0030380 A1*   1/2009   Binmoeller ............... 604/264

* cited by examiner

*Primary Examiner* — Melanie Hand
(74) *Attorney, Agent, or Firm* — Monument IP Law Group

(57) ABSTRACT

The embodiments of the present invention relate to an endoscopic system and accessories. In particular, the various embodiments relate to endoscopic systems in which an accessory comprises a multi-lumen device that is capable of quantitatively delivering at least a catheter, a balloon, and a needle to a site. The accessory is configured to allow for individual, independent control of its components. For example, in some embodiments, the needle and guidewire can be independently controlled. In addition, the needle may be retracted back into an inner lumen of the catheter body. Accordingly, during use, the accessory of the embodiments allows the user to maintain access to an incision site without having to exchange or remove accessories for various parts of the procedure.

13 Claims, 13 Drawing Sheets

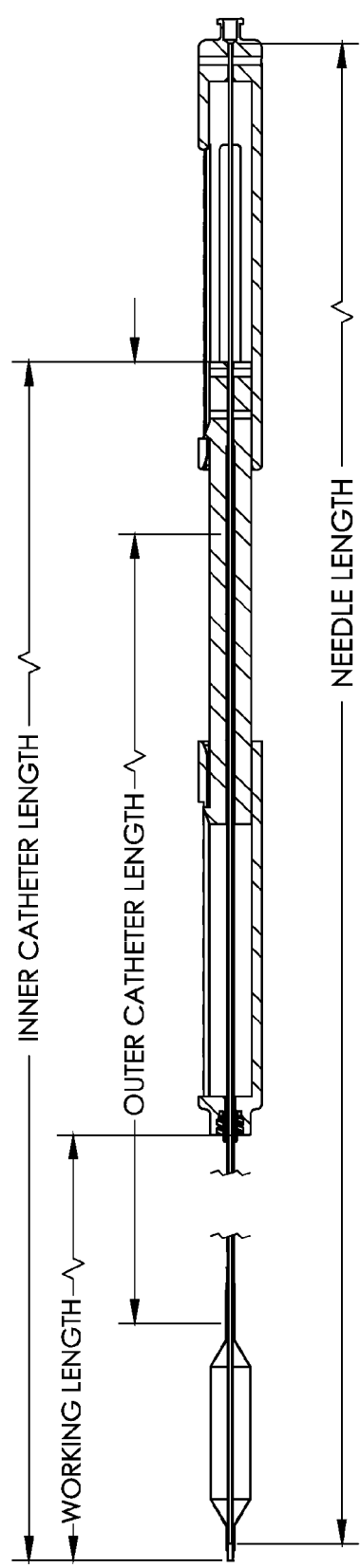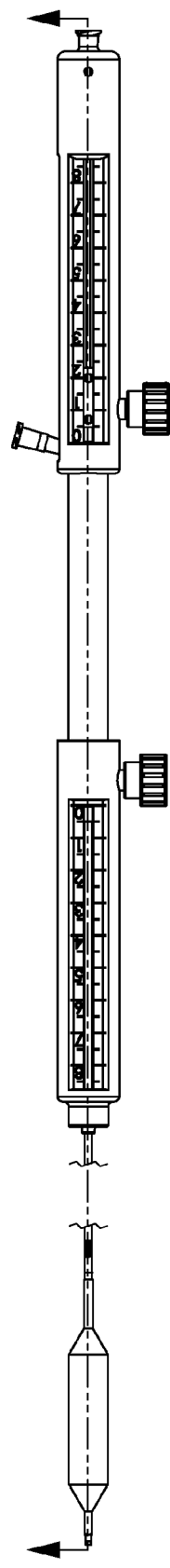
FIG. 10A
FIG. 10B
FIG. 10C

MULTI-LUMEN ENDOSCOPIC ACCESSORY AND SYSTEM

CROSS-REFERENCE TO RELATED APPLICATIONS

This application claims priority to U.S. Provisional Patent Application No. 61/230,175, filed on Jul. 31, 2009, entitled "COMBINATION ENDOSCOPIC ACCESSORY," by Abhitabh Patil et al., which is incorporated herein by reference in its entirety.

FIELD

The embodiments relate to endoscopic systems and methods, and more particularly, the embodiments relate to endoscopic accessories.

BACKGROUND

Endoscopy is a medical procedure in which an instrument is used to examine and treat the interior of a patient's organ, usually through a natural orifice. For example, endoscopes are commonly used to examine or treat a hollow organ or cavity of the body, such as the stomach.

Endoscopy procedures have become useful for treating, among other things, pseudocysts. Over 80,000 people are diagnosed with pancreatitis in the United States annually. The condition typically results in acute upper abdominal pain and can be life threatening as the pancreas loses its endocrine and exocrine functions. In many cases, pancreatitis physically manifests itself as a pseudocyst, which is a fibrous collection of fluid formed atop the organ.

An effective treatment for the condition is through cyst drainage. Drainage of the cyst can be required if the cyst persists and or grows in size to be greater than five centimeters in diameter. Traditionally, pseudocysts have been treated surgically, requiring a large open incision through the stomach or with an endoscopic procedure.

Conventionally, endoscopic surgery was performed with a needle knife to make an incision into the stomach. Unfortunately, this procedure increased the risk for internal bleeding through the cutting of blood vessels. As a result, typical procedures now use a balloon to dilate the track instead. This procedure is known as cystgastrostomy. This change has resulted in endoscopic transmural drainage of pancreatic pseudocysts to become common as it makes use of a natural orifice, the mouth, instead of making an external incision through the stomach.

A cystgastrostomy is a minimally invasive procedure used to drain a pancreatic cyst accessed endoscopically via the stomach wall. After identifying a cyst via ultrasound, a first endoscopic instrument or accessory is used to provide a hollow needle. The hollow needle is guided by an endoscope containing a thin guidewire and used to puncture through the stomach wall to access the pancreatic cyst. A puncture location is determined by an endoscopic ultrasound based on trying to avoid blood vessels and to prevent bleeding.

The current cystgastrostomy methods, however, require the full removal of the needle along the guidewire before the balloon can be positioned in the incision. The first instrument or accessory with the needle is removed and the conventional procedure requires leaving the guidewire at the site of the cyst.

Using a second endoscopic instrument or accessory, a surgical balloon is then fed along the guidewire. The balloon is used to dilate the incision. The balloon is then deflated and also removed along the guidewire.

Fluid from the cyst drains into the stomach through a natural pressure gradient. Two to three pigtail stents may be inserted to facilitate the drainage. The stents can be left in place for a few days and removed at a later time. The efficacy of the drainage is assessed during a post-op to ensure there is no infection from clogging of the stents.

As noted, the conventional methods and instruments require the full removal of the needle tip along the guidewire and the subsequent insertion of a balloon along the same guidewire. This requires an exchange of endoscopic instruments or accessories. In this exchange, there exists a relatively high level of risk of guidewire dislocation from the pancreatic cyst access site. Such a loss of access is a considerable setback during this procedure because a gastroenterologist is then forced to either relocate the incision, or repeat the echo ultrasound to determine another acceptable puncture location. Having to find a new location only increases the risk of a hemorrhage.

Accordingly, it may be desirable to improve the conventional endoscopic procedures, such as those mentioned above.

SUMMARY

In accordance with an embodiment of the present disclosure, a method comprises: endoscopically introducing a multi-lumen catheter comprising an integral inflatable balloon and housing a hollow needle within a lumen; puncturing an organ wall, with the hollow needle, to create access to a desired site within the organ; advancing a guidewire within a lumen of the hollow needle to the desired site; retracting the hollow needle from the desired site; advancing the balloon into the desired site along the guidewire; inflating the balloon; and removing the multi-lumen catheter.

In accordance with an embodiment of the present disclosure, an endoscopic accessory comprises: a multi-lumen catheter having a proximal and distal end; an inflatable balloon affixed to the distal end of the catheter in fluid communication with a first lumen; and a hollow needle housed within the multi-lumen catheter for independent movement relative to the inflatable balloon; wherein the hollow needle is configured to be extended and retracted in conjunction with a guidewire at a desired site within a patient.

Additional features of the embodiments will be set forth in part in the description which follows, and in part will be obvious from the description, or may be learned by practice of the invention. The features of the embodiments can be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate some embodiments of the invention and together with the description, serve to explain the principles of the invention. In the Figures:

FIGS. 10A-10C shows a side view of an endoscopic accessory for an embodiment of the present invention.

DESCRIPTION OF THE EMBODIMENTS

Figure 1:
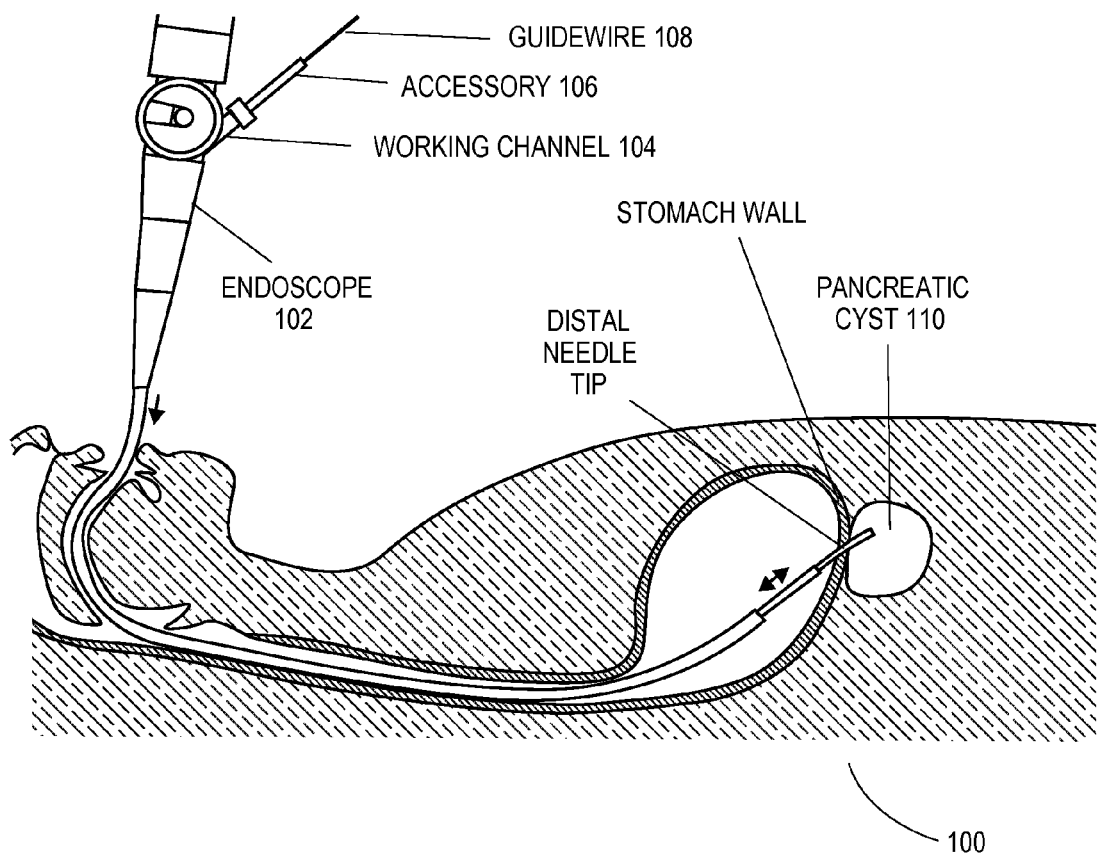
FIG. 1 illustrates an exemplary endoscopic procedure in which the embodiments may be employed.

The embodiments of the present invention relate to an endoscopic system and accessories. In particular, the various embodiments relate to endoscopic systems in which an accessory comprises a multi-lumen device that is capable of quantitatively delivering at least a catheter, a balloon, and a needle to a site. The accessory is configured to allow for individual, independent control of its components. For example, in some embodiments, the needle and guidewire can be independently controlled. In addition, the needle may be retracted back into an inner lumen of the catheter body. Accordingly, during use, the accessory of the embodiments allows the user to maintain access to an incision site without having to exchange or remove accessories for various parts of the procedure.

For purposes of illustration, the embodiments are described for use as an endoscopic accessory for drainage of pancreatic cysts. It will be apparent to those of skill in the art that the accessory is readily adaptable for other procedures including other endoscopy procedures as well as laparoscopy procedures. The embodiments may be used with virtually any type of minimally invasive procedure.

Accordingly, all dimensional measurements disclosed here are for exemplary purposes only and can be changed, as needed depending upon the type of procedure and the relative area within which the device will be used. Furthermore, all dimensions disclosed herein are approximate, although it is noted that this is a precision instrument and relatively tight controls may be employed to ensure proper operation.

To assist in explaining the embodiments, the present disclosure describes a procedure involving drainage of pancreatic cysts. For such a procedure, the endoscopic working channel may have a diameter of about 3.1 mm. Accordingly, the accessory of the embodiments is configured for use within this diameter. However, as the diameter of the working channel varies so can the dimensions of the accessory.

The endoscopic accessory described herein comprises a multi-lumen catheter, balloon, and hollow needle. In some embodiments, the accessory is adapted for use in cystgastrostomy for facilitating the drainage of pancreatic cysts. Additional components may also be used to enhance the usability of the device. In particular, a connection valve for splitting the multi-lumen at the proximal end for individual control of each lumen may be used. An extension mechanism for controllably advancing the balloon may also be provided.

Although any suitable catheter design may be employed, a catheter having multiple lumens is described. The present disclosure will generally refer to the accessory and catheter as having a proximal end nearest the endoscope and a distal end nearest the procedure site.

In general, the procedure for cystgastrostomy may comprise having the hollow needle pass through and within an inner lumen (the needle lumen). In turn, the guidewire passes through and within the hollow needle. The balloon is affixed to the exterior wall of the distal end of the inner lumen and at the balloon's proximal end to the exterior wall of the outer lumen, i.e. the external catheter wall. In this manner, the internal volume of the balloon is in fluid communication with the outer lumen (the fluid lumen), through which a filling medium is passed to fill the balloon and removed to deflate the balloon.

The filling medium is chosen according to the procedure and its location. The medium should be chosen so as to be relatively safe, in the event the balloon should inadvertently rupture and the filling medium be released. Suitable filling media include air, other gas, sterile water, sterile saline, and the like. For example, for a pancreatic cystgastrostomy, sterile water or saline may be employed as the filling medium, since any leakage will occur in the stomach, which will readily accept the liquid.

The hollow needle can be any type of hollow needle suited to the specific procedure. The hollow needle is sized for ease of removal through the inner lumen while being able to make an appropriately sized incision. As will be recognized by those of skill in the art, the needle may have a tip that is sharp enough for piercing. For example, the needle may be sufficiently sharp to pierce the stomach lining for use in a pancreatic cystgastrostomy, the stomach lining. The piercing facilitates access to the pancreatic cyst beyond the stomach wall.

A guidewire may be provided for advancing through the hollow needle. The guidewire is affixed to the treatment site (e.g. cyst) so that it may be used to guide placement of further articles, such as stents, at the treatment site. Any suitable guidewire may be used.

In accordance with some embodiments of the invention, once the incision is made, the balloon catheter can be moved distally into the incision made by the needle and then inflated. This can be accomplished by means of an extension mechanism designed for controllably and precisely advancing the balloon the desired depth into the incision.

The embodiments thus have certain advantages over known procedures and instruments. For example, current procedures and instruments must rely almost solely on the skill of the surgeon, who operates largely by "feel." In contrast, employing the extension mechanism of the embodiments allows for accurate and informed advancement of the balloon.

In the embodiments, the distance from the needle at the time of puncture to the balloon can be quantitatively and continuously tracked. Thus, the surgeon can know precisely how far the balloon will need to be advanced to be in appropriate position to expand the incision. In many cases, the incision will be centered along the length of the balloon, although this is not necessary.

In some embodiments, the multi-lumen catheter exits the proximal end of the working channel of the endoscope and runs through an extension mechanism or connection valve. The extension mechanism can be a telescoping device designed to provide added control to the gastroenterologist while pushing the entire catheter into the cyst.

The connection valve is designed to separate the multiple lumens for individual control by the surgeon. The extension mechanism and connection valve may be integrated into a single component in some of the embodiments.

The extension mechanism may comprise an inner and an outer cylinder in a slidable arrangement with each other. In some embodiments, the inner cylinder may have a diameter of about 15.5 mm and connects to the working channel port using a female connection. A channel of about 3.0 mm may then provided to be the same size as the working channel and is preserved through the cylinder.

A hollow outer cylinder, with an outer diameter ("OD") of about 20 mm and an inner diameter ("ID") of about 16 mm, may accept the inner cylinder. Mating projections and grooves may be provided on the outer surface of the inner cylinder and the inner surface of the outer cylinder to minimize or prevent axial rotation.

In some embodiments, the inner cylinder has a length of about 10 cm (i.e., the outer can have an equivalent channel) allowing an extension of about 8 cm. Calibrations on the inner cylinder along with a viewing port, such as a circular cutout on the outer cylinder, can allow for the physician to have quantitative control on the degree of insertion of the entire catheter into the incision site. A lock ring can also be provided to secure the position with the tightening of it to the inner cylinder using a bolt.

The proximal portion of the outer cylinder can serve as or be adapted for connection to a connection valve splitting the needle and fluid lumen of the catheter. The valve can be cast out of molten plastic around the proximal tip of the lumen. The needle channel can thus continue out through the proximal end and a fluid channel can run out of the side of the valve (e.g., about 2 cm from the end) for communication with a fluid source.

In some embodiments, the splitting of the lumen channels can take place over a distance, such as about 6 cm. Additional features of the valve allow for the connection of existing controllers. For example, at the top of the valve (e.g., around the needle channel), a reproduced working channel port can allow an existing controller to be secured.

A fitting, such as a luer lock connection, can be used extending from the fluid channel to allow fluid to be pumped through the channel using fluid source controller. For example, water can be pumped and removed through the fluid channel via a balloon dilator. Once in position, the balloon can be inflated to enlarge the incision to facilitate placement of one or more stents or other instruments.

Once the incision is enlarged, the balloon is deflated, and the catheter removed along the guidewire. The guidewire is left in place for further treatment, such as insertion of stents for facilitating drainage of the cyst. Because a floating (concentric) inner lumen is unnecessary, a more traditional and available semi-circle double lumen or other double lumen construction can be used.

A catheter is provided with multiple lumens each defined by a catheter wall. A first lumen is provided for housing the hollow needle for movement therein. The second lumen is used or adding and removing filler medium to inflate and deflate the balloon respectively. The balloon volume is again in fluid operation with the second lumen.

The proximal end of the balloon may be affixed to the outer wall of the catheter, and affixed at its distal end such that filler medium leaves the second lumen and enters the balloon volume thereby inflating the balloon. This embodiment can provide stiffness and improved durability due to increased wall thickness. The balloon may be attached via a weld. The water channel of the lumen seals off at the distal end and makes dilation possible while keeping the needle channel intact.

Reference will now be made in detail to the present embodiments, examples of which are illustrated in the accompanying drawings. Wherever possible, the same reference numbers will be used throughout the drawings to refer to the same or like parts.

FIG. 1 illustrates an exemplary endoscopic system and procedure in which the embodiments may be employed. In particular, an endoscopic procedure for treating a pancreatic pseudocyst is shown to illustrate the principles of the embodiments.

As shown, a patient 100 is being treated with an endoscope 102. The endoscope 102 provides a working channel 104. At the proximal end, an accessory 106 may then be attached to the endoscope 102 in order to access the working channel 104. During a procedure, a guidewire 108 may be fed through the accessory 106 to access the site at the distal end. At the distal end, the accessory 106 may provide a needle tip 108 that can pierce the patient's stomach wall and access the pancreatic cyst 110 via the patient's abdominal cavity.

Figure 2:
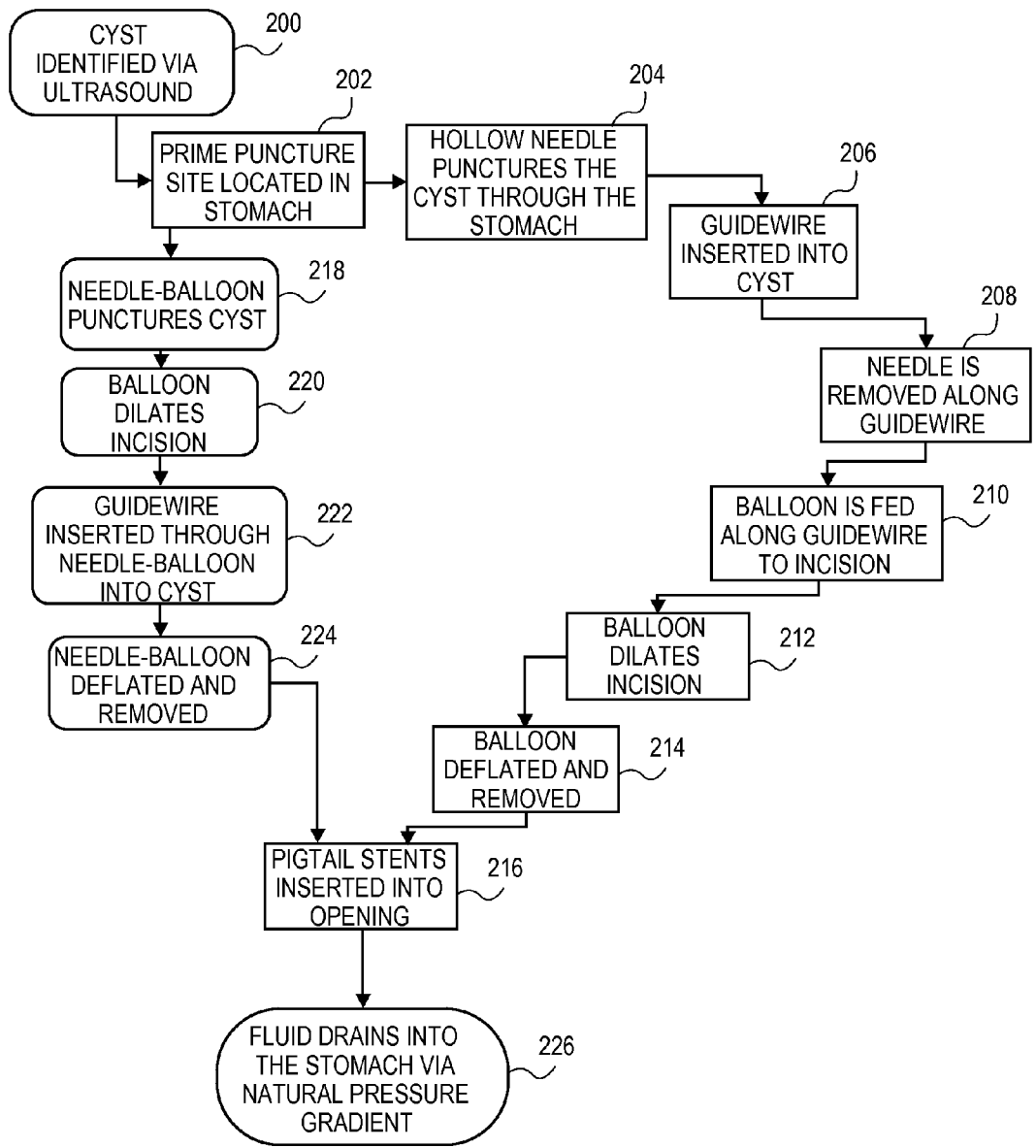
FIG. 2 illustrates some exemplary process flows by the embodiments.

FIG. 2 illustrates some exemplary process flows by the embodiments that may be employed to treat a pancreatic cyst or pseudo cyst. As shown, two processes may be used by the embodiments to treat a pancreatic cyst or pseudo cyst. For purposes of illustration, the process flows of FIG. 2 are described with reference to accessing the cyst near the stomach through a patient's abdominal cavity.

At phase 200, the cyst 110 is identified. For example, the cyst 110 may be identified using an ultrasound image or other suitable diagnostic procedure.

At phase 202, a user, such as a surgeon or gastroenterologist, may determine and select a desired or prime puncture in the patient's stomach. The site may be determined and selected based on a variety of criteria, such as avoidance of blood vessels and likelihood of bleeding, as well as the location of the cyst.

In a first embodiment, at phase 204, the user may utilize the accessory 106 to insert a hollow needle tip into the stomach wall and puncture the cyst 110 through the wall of the patient's stomach.

Next, at phase 206, the user may insert a guidewire 108 through the endoscope 102 into the cyst 110. In phase 208, the hollow needle is then removed along the guidewire 108.

In phase 210, a balloon (not shown in FIG. 1) is fed along the guidewire 108 into the incision previously made by the hollow needle tip. In phase 212, the user then inflates the balloon to dilate the incision. For example, the balloon may be inflated with a suitable medium, such as saline.

In phase 214, the user then deflates the balloon and removes it from the incision site. In phase 216, the user then may place one or more pigtail stents (not shown in FIG. 1) into the dilated opening of the stomach wall. The pigtail stents may be used, for example, to maintain the opening in the stomach and allow the cyst to drain over time.

Alternatively to phases 204 to 214, another embodiment of the present disclosure may utilize a shorter procedure. For example, in phase 218, a user, such as a surgeon, may insert a hollow needle into the patient's stomach wall and puncture the wall to access the cyst 110.

In phase 220, the user may then insert the catheter and balloon and inflate the balloon to dilate the incision made previous by the needle. In phase 222, the user then inserts a guidewire 108 through the hollow needle into the cyst 110.

In phase 224, the user then allows the balloon to deflate and retracts the catheter from the site. As will be recognized and further described in the present disclosure, this procedure allows the user to maintain consistent access to the site without changing endoscopy instruments or accessories.

Figure 3:
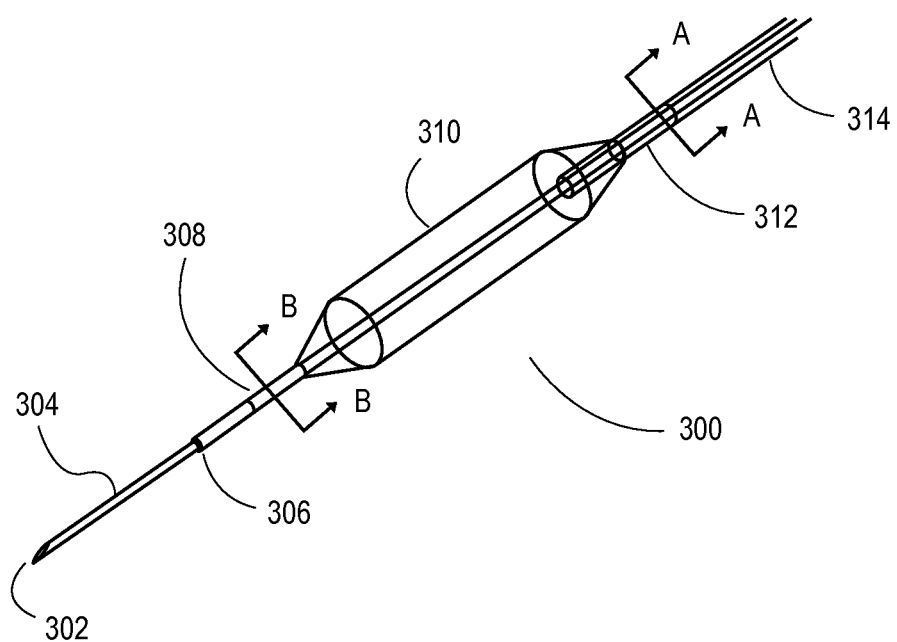
FIG. 3 shows an exemplary perspective view of a distal end of an embodiment of the present invention.
Figure 4:
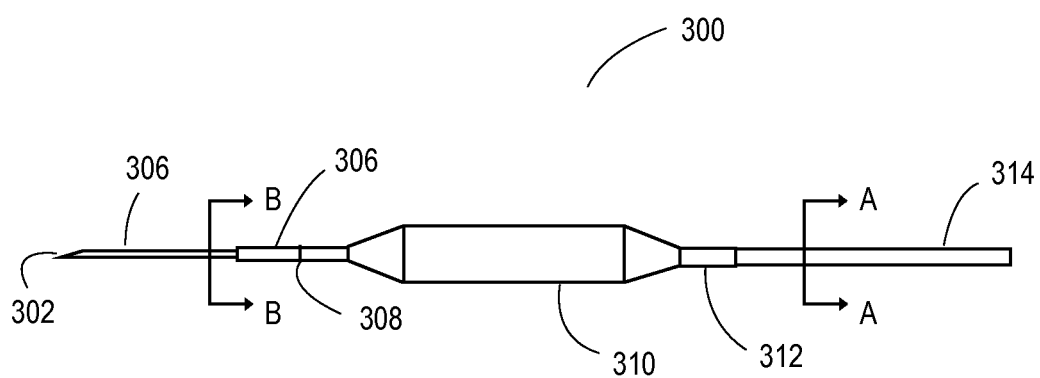
FIG. 4 shows an exemplary side view of a distal end of an embodiment of the present invention.

FIG. 3 shows an exemplary perspective view of a distal end 300 of an embodiment of the present invention. FIG. 4 shows an exemplary side view of the distal end 300.

As shown, at the distal end 300, a hollow needle shaft 304 terminates at a hollow needle tip 302.

Although the characteristics of the entire endoscopic accessory 106 and its component parts can vary depending upon its intended use, for a pancreatic gastrostomy, the hollow needle may be a 19 gauge needle (or other suitable gauge), have a 0-3.149 inch needle extension, and able to house a 0.035 inch guidewire 108. In addition, sheath of the hollow needle sheath may be approximately 140 cm in length and may have a specimen notch of about 20 mm.

In one embodiment, the needle is made of medical grade stainless steel ($OCr_{19}Ni_9$) that has a high tensile strength to prevent breakage during puncture. The needle may also be relatively ductile.

The needle shaft 304 may be contained within an inner lumen (or needle lumen or needle channel). As shown, at distal end 300, the needle shaft 304 may exit the inner lumen at neck 306 to puncture and access a desired site in patient 100.

A balloon 310 may also be provided at distal end 300. The balloon 310 may be about 0.315-0.472 inch in diameter for inflation (8-12 mm, 24-36 French) and support inflation pressures between about 3 and 9 ATM. In the embodiments, the balloon 310 is sized depending upon its intended use. For about, in one embodiment the balloon 310 can be about 4 cm in length. In other embodiments, the balloon 310 may be about 8 cm in length. The balloon 310 may also have a radio-opaque distal end to make distinguishable during fluoroscopy. The balloon 310 may a length that can stretch along the tract of a puncture, for example, in the stomach wall to cyst 110 (such as, approximately 0.275 inches-0.394 inches).

The balloon 310 may be constructed from PEBAX, or other biocompatible polymer (biocompatible polymer composed of rigid polyamide blocks and soft polyether blocks). In general, any high strength, resilient material with great elasticity can serve as a material for balloon 310. The material may also be a soft material for easy machining and maneuverability through the puncture site. Furthermore, a biocompatible surgical lubricant can be used to coat balloon 310 to reduce friction during puncture or the procedure.

Of note, the inner or needle lumen extends slightly beyond the outer lumen at the distal end 300. Thus, the balloon 310 may be in fluid communication to the fluid lumen at the proximal end of endoscope 106 and to the needle lumen at the distal end 300. The result of this is a seal that allows water to flow into the balloon 310, but not out of the other side.

The balloon 310 may be heat welded (e.g., with a total length of about 4-8 mm) onto the extended needle channel (1.00 mm from the tip) at the distal end and onto the outer edge of the lumen at the proximal end. The result of this is a seal that allows water to flow into the balloon but not out of the other side. The use non-light weight walls and non-floating lumen (despite the extension of the needle channel) also may provide sufficient axial rigidity to push the catheter into the incision site. The distal tip of the exposed lumen may have a gradient slope allowing for a smooth transition of increasing diameters. Also, the balloon 310 may be trained to deflate into a circular shape with a diameter of less than 3.1 mm.

For example, as shown, the balloon 310 may be attached to the outer wall of the inner lumen at 308. In some embodiments, the balloon 310 is welded to the outer wall of the inner lumen at 308. Of course, other attachment means, such as glue, may be used to bond the balloon 310.

The balloon 310 is also attached to the outer wall of an outer lumen 314 (or catheter fill lumen or water fill lumen). As shown, the balloon 310 may be welded, glued, etc. to the outer wall of the outer lumen 314 along a length 312. Accordingly, by being attached to the outer walls of both the inner lumen and outer lumens, the balloon 310 may be in fluid communication with the accessory 106 at the proximal end of the endoscope 102.

Figure 5:
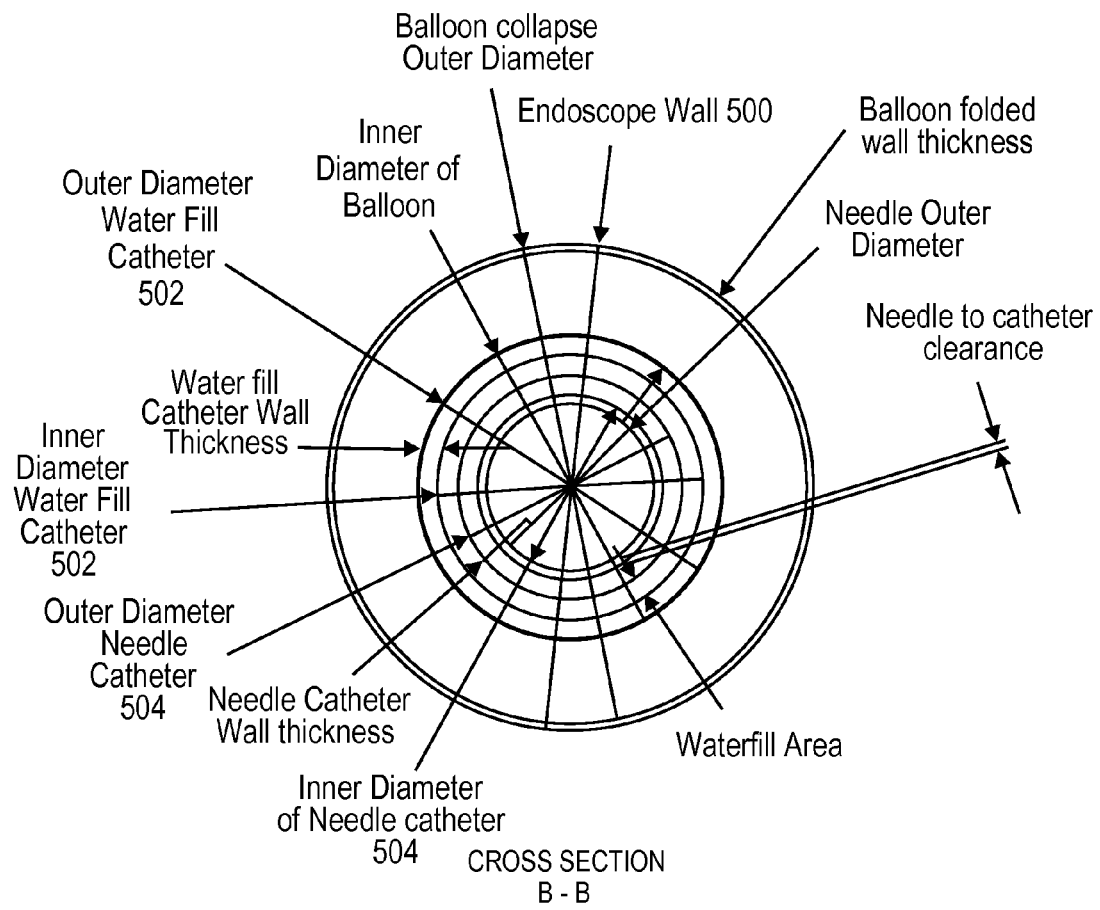
FIG. 5 shows an exemplary cross section B-B of a tube for an endoscope for an embodiment of the present invention.
Figure 6:
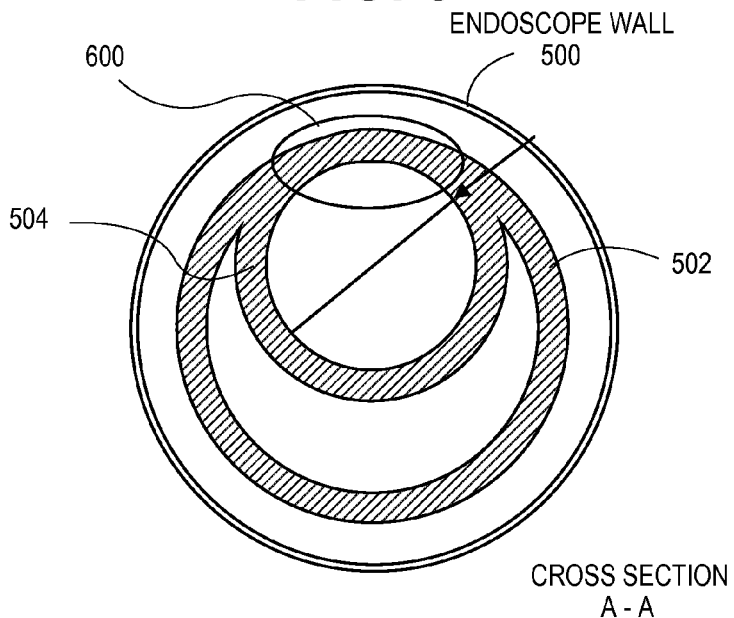
FIG. 6 shows an exemplary cross section A-A of a tube for an endoscope for an embodiment of the present invention.

FIGS. 5 and 6 are provided to show different exemplary cross sections that may be employed along the length of the catheter from endoscope 106. As will be further described, the embodiments may employ a "floating" concentric cross section design (e.g., cross section B-B shown in FIG. 5) and an "attached" cross section design (e.g., cross section A-A shown in FIG. 6).

As shown in FIG. 3, the cross section B-B may be employed distally beyond the balloon 310. This design may be employed to ensure maximum freedom of motion of the components controlled by accessory 106 and clearances. In other locations, such as proximally before the balloon 310, the cross section A-A may be employed to provide enhanced rigidity, e.g., to aid in puncture strength and to minimize crumpling of the balloon 310 during puncture. In one embodiment, the length of the endoscope proximally before the balloon 310 employs cross section A-A. In other embodiments, the cross section B-B is employed at discrete points along the length of the catheter. These discrete points may be at regular intervals or spaced apart depending upon various factors, such as bending radius, etc. The cross section B-B may be constructed by heat bonding or welding the inner catheter 504 to the inner wall of the outer catheter 502.

FIG. 5 shows an exemplary cross section B-B of a tube for an endoscope for an embodiment of the present invention. As shown, the embodiments may employ a multi-lumen design. For example, in FIG. 5, a double lumen embodiment is shown. The double lumen embodiment shown provides a path to pull the needle out (the inner lumen or needle lumen) and providing a method to inflate the balloon (the water fill catheter). In general, the endoscope tube 500 may house a first (or water fill) catheter 502. Water fill catheter 502 provides an outer lumen for water fill of the balloon 310. In addition, catheter 502, within its lumen, may house an inner (or needle) catheter 504.

In the embodiment shown, the needle lumen has a diameter of 1.57 mm in order to house the 19 gauge needle. The fluid lumen, when round, may be about 2.9 mm in diameter, or otherwise has adequate space to allow water (or other filling media) to flow through for inflation of the balloon. In addition, this 2.9 mm diameter allows for easy access into the 3.1 mm endoscope catheter. Both catheters 502 and 504 may be constructed from PTFE/Teflon tubing. Other embodiments may incorporate PEBAX tubing. The use of a double lumen can also result in a more rigid catheter that is able to more easily push into the incision site. The inside catheter adds sufficient stiffness to the design while still keeping it maneuverable.

FIG. 6 shows an exemplary cross section A-A of a tube for an endoscope for an embodiment of the present invention. As shown, the inner catheter 504 may be attached or bonded to the inner wall of the outer catheter 502 at location 600. As noted above, this attachment of the catheters 502 and 504 may be employed to improve the rigidity of the catheter overall and to avoid excessive movement of the catheters 502 and 504 relative to each other.

Figure 7:
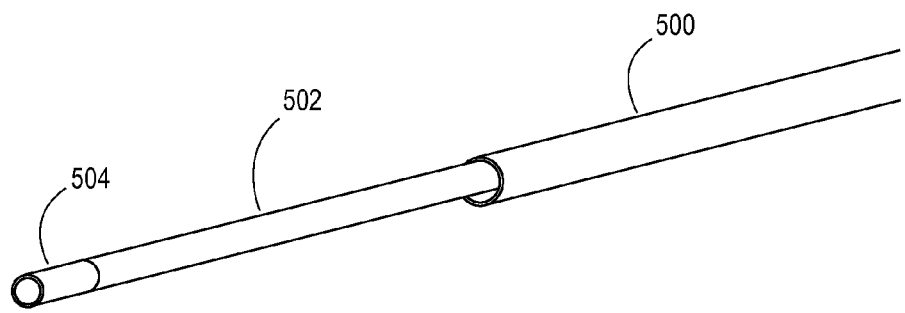
FIG. 7 shows a perspective view of the double lumen design of the embodiments.

FIG. 7 shows a perspective view of the double lumen design of the embodiments. As shown, the endoscope catheter 500 may house a water fill catheter 502 within its lumen. In addition, needle catheter 504 may be housed within the water fill catheter 504 to provide an inner (or needle) lumen.

Figure 8:
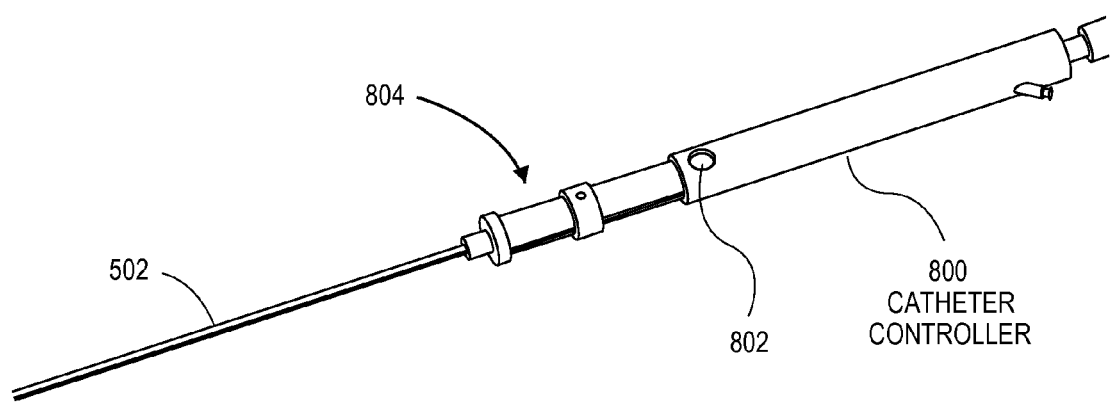
FIG. 8 shows a portion of an endoscopic accessory for an embodiment of the present invention.

FIG. 8 shows a portion of an endoscopic accessory for an embodiment of the present invention. As shown, the endoscope accessory 106 may comprise at its front end a catheter (or balloon) controller 800, a locking mechanism 802, and an attachment port 804. Catheter controller 800 is described further below. Attachment port 804 and locking mechanism 802 provides a fitting (such as a luer lock) and sealing mechanism to secure accessory 106 to the working channel 104 of the endoscope 102.

Figure 9:
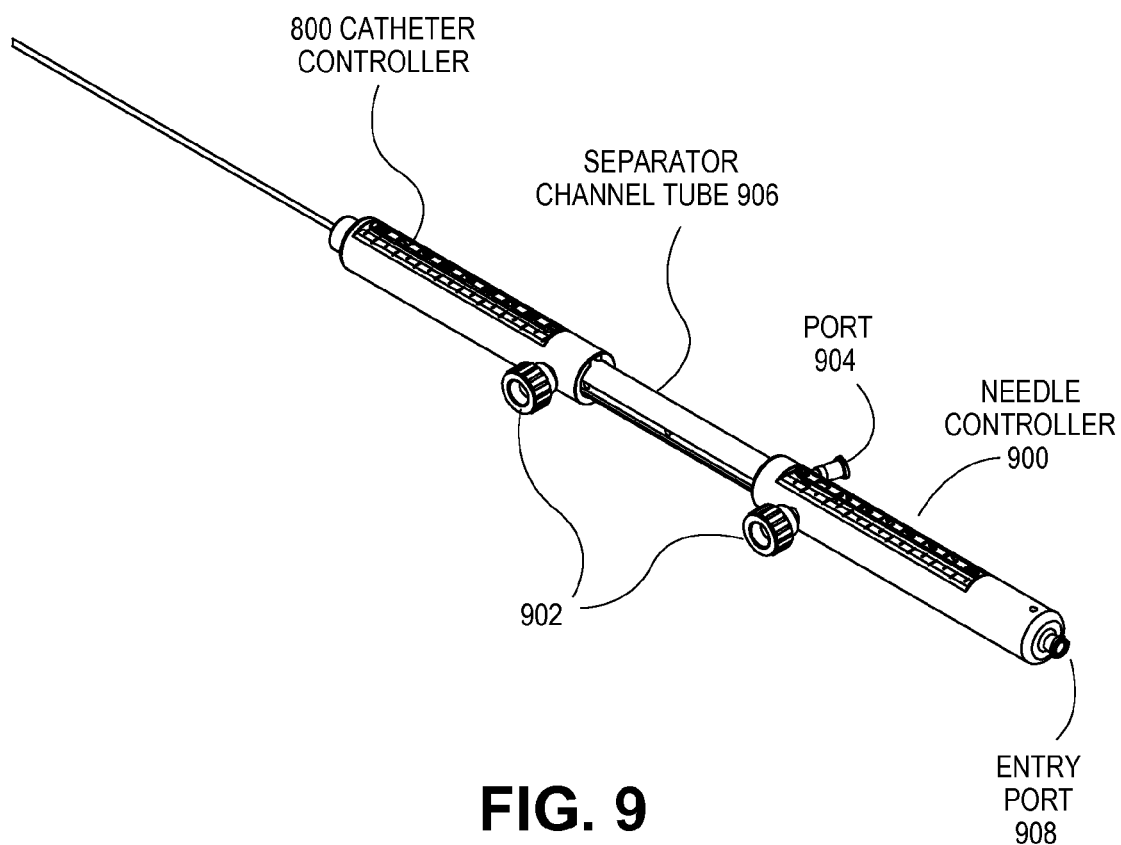
FIG. 9 shows a perspective view of an endoscopic accessory for an embodiment of the present invention.

FIG. 9 shows a perspective view of an endoscopic accessory 106 for an embodiment of the present invention. FIGS. 10A-C show a side view of an endoscopic accessory for an embodiment of the present invention.

As shown, the accessory 106 may comprise multiple controllers. This multi-controller design allows for procedures, such as a pancreatic cystgastrostomy, to be performed without having to exchange or use multiple accessories and instruments.

For example, as shown, the accessory 106 may comprise a catheter controller 800 at its front end a needle controller 900 at its back end. In the embodiment shown, the accessory 106 employs a sliding mechanism that allows the user to selectively control the needle and balloon at different times both independently and without having to change accessories.

As also shown, the accessory 106 may comprise locking nuts 902 to selectably secure controllers 800 and 900 at a specific location along its slidable length. Although a sliding mechanism is shown, the embodiments may employ other types of mechanical motion, such as a rotary or screw based motion.

Accessory 106 further comprises ports 904 and 908. Port 904 may be provided to allow for media, such as water, saline, etc., to be injected into the balloon 310 at the distal end 300. Port 908 provides an entry, for example, of guidewire 108 and a needle (not shown) by the user.

Separator channel tube 906 provides for mechanical travel for the controllers 800 and 900. In addition, the separator tube 906 may provide a connector valve (not shown). To ensure that each lumen functions respectively, a connector valve splits the double lumen design into respective components. The valve has one section that connects to the fluid lumen and another that connects to the needle lumen.

For the purposes of the drainage of a pancreatic pseudocyst, the fluid lumen can be connected to a water gun for example at port 904, while the needle lumen will be connected to controller 900 that allows for minute control over the puncturing needle. The distal end of the valve is may be large enough to securely fasten onto the double lumen. In one embodiment, the entire length of the valve is 60 mm with an outer diameter of 25 mm and an inner diameter of 2.8 mm.

Figures 11A, 11B:
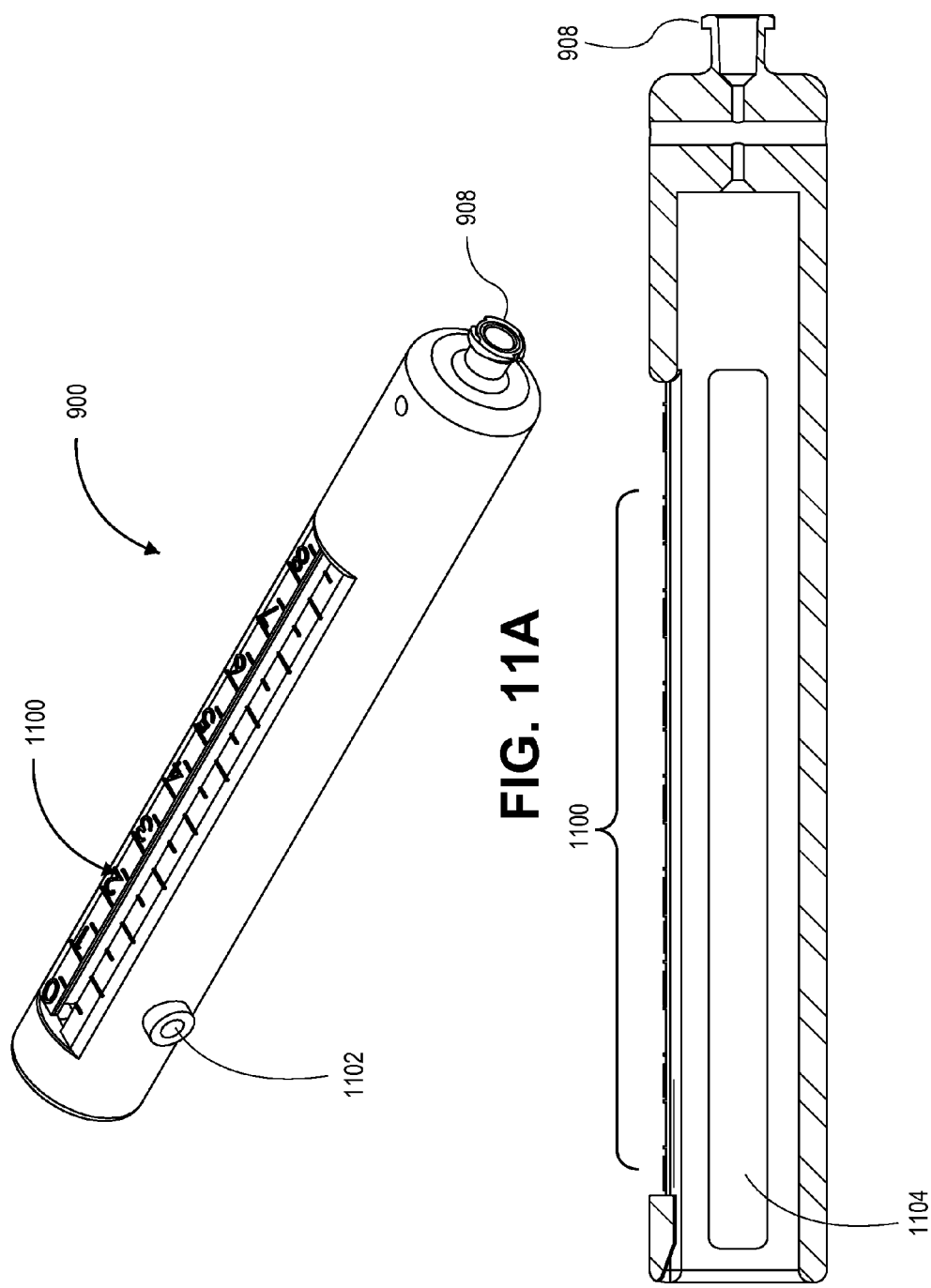
FIGS. 11A and 11B show an exemplary needle controller portion of an endoscopic accessory for an embodiment of the present invention.

FIGS. 11A and 11B show an exemplary needle controller portion 900 of an endoscopic accessory for an embodiment of the present invention. As shown, the needle controller 900 may comprise a ruler 1100 and a locking mechanism 1102.

Ruler 1100 provides the user a visual indication of the amount of travel that has been used for moving the needle. The ruler 1100 may provide various units of measure, such as inches, cm, mm, etc., depending on the procedure and amount of travel desired. In addition, ruler 1100 may be marked to indicate various thresholds, such as minimum travel, maximum suggested travel, and the like.

Locking mechanism 1102 provides a port for securing the needle controller 900, if desired. For example, mechanism 1102 may be designed to accommodate a bolt, such as the locking bolt 902 shown in FIG. 9. As also shown in FIG. 11B, the needle controller 900 may comprise a slot 1104 to accommodate port 904 (as shown in FIG. 9).

Figure 12A:
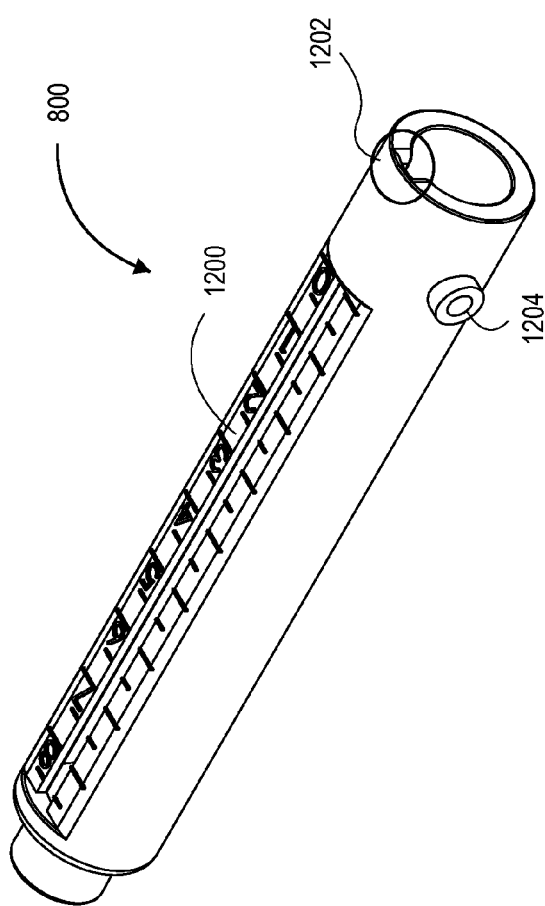
FIGS. 12A and 12B show an exemplary catheter controller portion of an endoscopic accessory for an embodiment of the present invention.
Figure 12B:
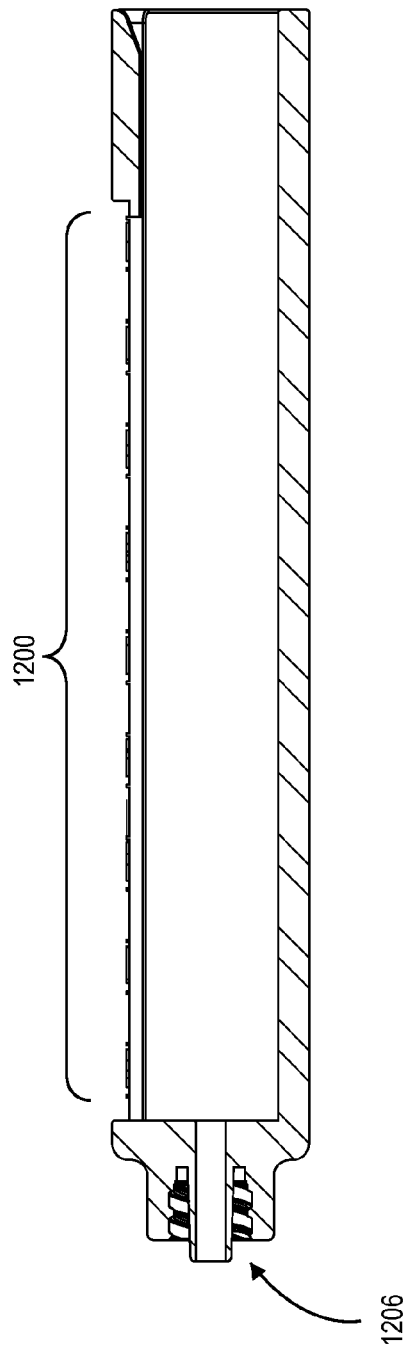

The exemplary characteristics of the needle controller may include:
A push/pull extension mechanism to control needle extension;
Allow for extension of about 4 inches;
Handgrips for ease of control;
A first cylinder: 15 mm
A second cylinder: 12 mm
A T Handle: 65 mm width, 10 mm height and 5 mm depth
A base Handle: 20.05 mm width 6 cm length
The needle controller may be calibrated to ensure accurate movement of the needle;
A guidewire access point 908 of about 1.4 mm
A calibrated movement ruler in cm reflecting needle extension
The tip of the controller connects the extended inner lumen
Internal Components of Needle Controller may comprise:
A metal casing (surrounding proximal needle sheath): 1.58 mm FIGS. 12A and 12B show an exemplary catheter controller portion 800 for an embodiment of the present invention. As shown, the catheter controller 800 may comprise a ruler 1200, an alignment slot 1202, a locking mechanism 1204, and a fitting 1206.

Ruler 1200 provides the user a visual indication of the amount of travel that has been used for moving the catheter having balloon 310. The ruler 1200 may provide various units of measure, such as inches, cm, mm, etc., depending on the procedure and amount of travel desired. In addition, ruler 1200 may be marked to indicate various thresholds, such as minimum travel, maximum suggested travel, and the like.

Alignment slot 1202 provides a slot to maintain the radial alignment of the controller 800 during its use. Of note, needle controller 900 may also comprise a slot that is similar to slot 1202.

Locking mechanism 1204 provides a port for securing the needle controller 900, if desired. For example, mechanism 1204 may be designed to accommodate a bolt, such as the locking bolt 902 shown in FIG. 9.

Fitting 1206 provides the necessary physical structure to couple the accessory 106 to the working channel 104. Such fittings are well known to those skilled in the art.

Figure 13:
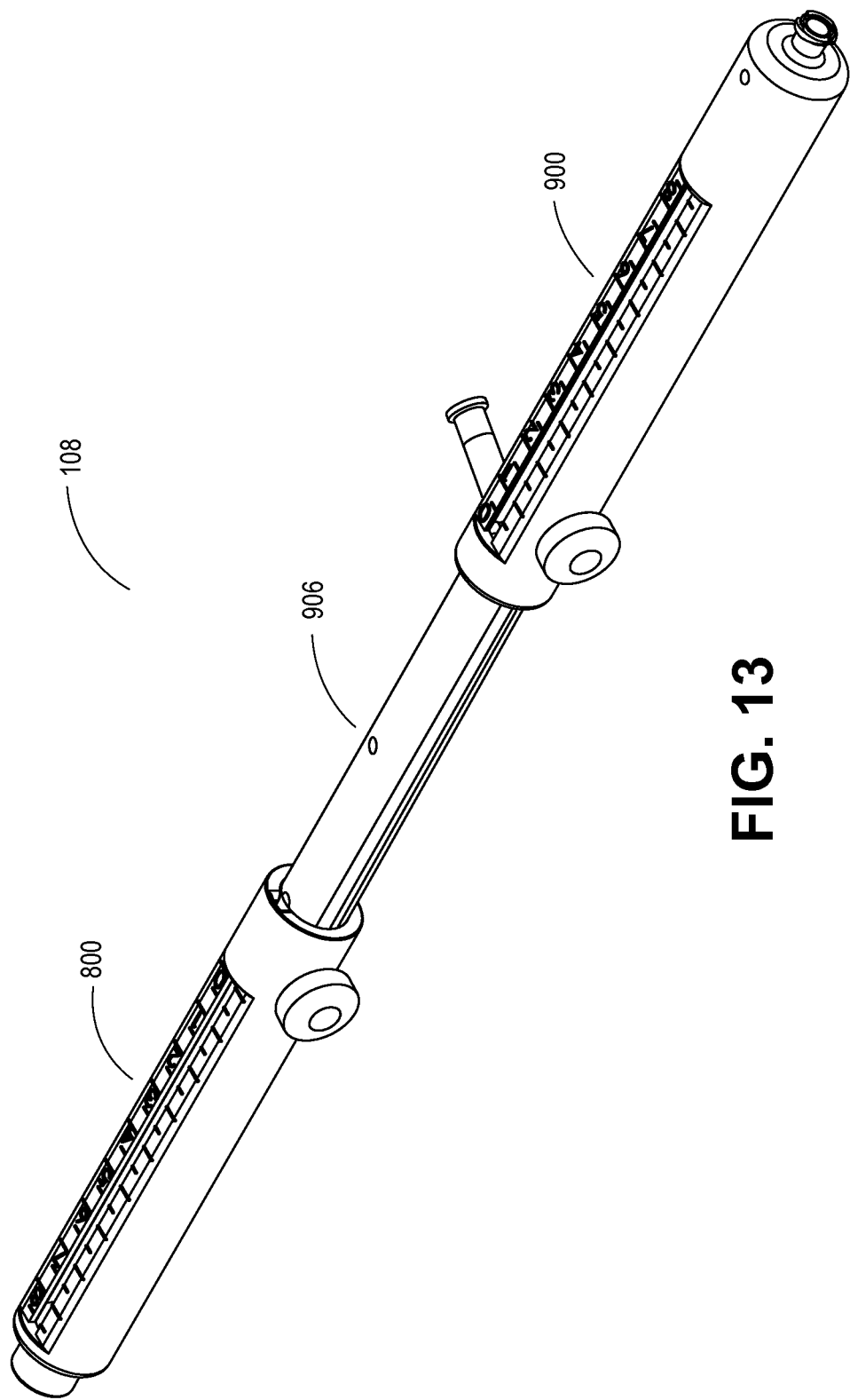
FIG. 13 shows another perspective view of the endoscopic accessory for an embodiment of the present invention.

FIG. 13 is provided to show another perspective view of the endoscopic accessory for an embodiment of the present invention. As noted, the distal end and proximal ends of the device will be connected by a double lumen, the characteristics of which may include: a needle lumen with dimension of 1.575 mm which houses hollow needle; a fluid lumen with about a 2.9 mm diameter that serves as a water channel, or volume suitable for proper inflation; a wall thickness of about 0.127-0.200 mm or smaller as desired.

Below are some exemplary characteristics of the catheter-controller connection valve. The valve splits the distal catheter tubing into two separate tubes to be sent to distinct controllers. A slot insertion of outer lumen (fluid lumen) to prevent water leakage. Two proximal channels are provided: one for water travel, one for needle control.

In one embodiment, the multi-lumen design allows for two functions: providing a path to pull the needle out and providing a method to inflate the balloon. The multi-lumen has a total diameter of 2.9 mm, allowing for sufficient clearance to maneuver through a 3.1 mm working channel of an endoscope. A cross section of the lumen reveals dual channels. A circular channel, sharing a wall with the outer edge of the lumen, has a diameter of 1.575 mm in order to house the 19 gauge needle (and potentially any additional needle sleeves). An exaggerated semicircular channel makes up the remaining portion of the lumen (separated by the outer wall of the lumen and the inner wall of the needle channel). All walls of the lumen have a uniform thickness of 0.200 mm, creating a large enough water channel to allow for sufficient flow. The needle channel can be advanced such that it extends past the water channel a sufficient length, for example, to attach the balloon 310.

Figure 14A:
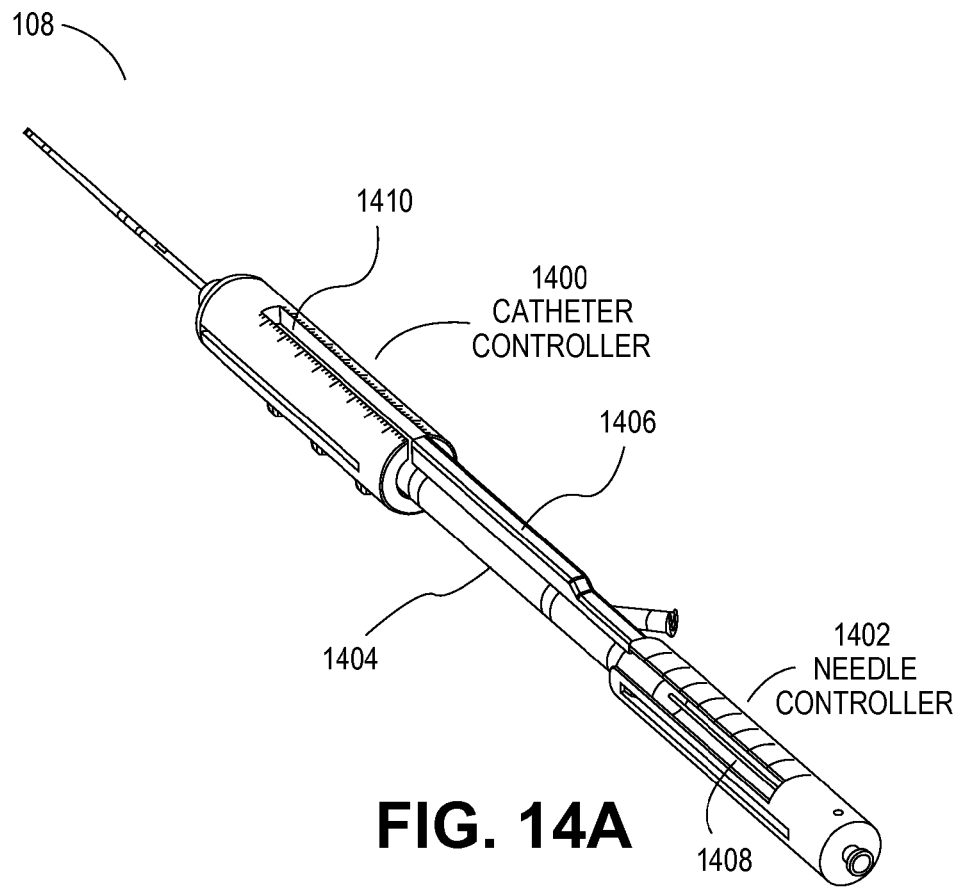
FIGS. 14A and 14B show perspective views of an endoscopic accessory for another embodiment of the present invention.
Figure 14B:
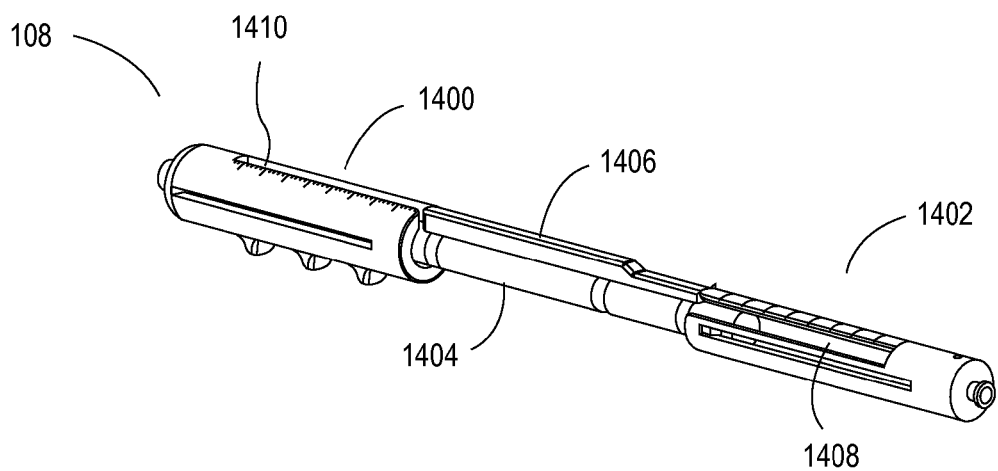

FIGS. 14A and 14B show perspective views of an endoscopic accessory for another embodiment of the present invention. In the embodiment shown, the endoscopic accessory 106 may employ a locking bar mechanism. As shown, the accessory 106 may comprise a catheter controller 1404 and a needle controller 1402. The controllers 1400 and 1402 may be connected together via a separator channel tube 1404.

In this embodiment, the tube 1404 comprises a locking bar 1406. For example, during operation, the user may rotate either controllers 1400 or 1402 such that guide slots 1408 and 1410, respectively align with locking bar 1406. When not aligned, the controllers 1400 and 1402 are held in place and prevented from moving.

In some embodiments, the locking bar 1406 is configured to allow only one controller at a time to move. In other embodiments, the locking bar 1406 allows both controllers to move simultaneously when aligned.

Figure 15:
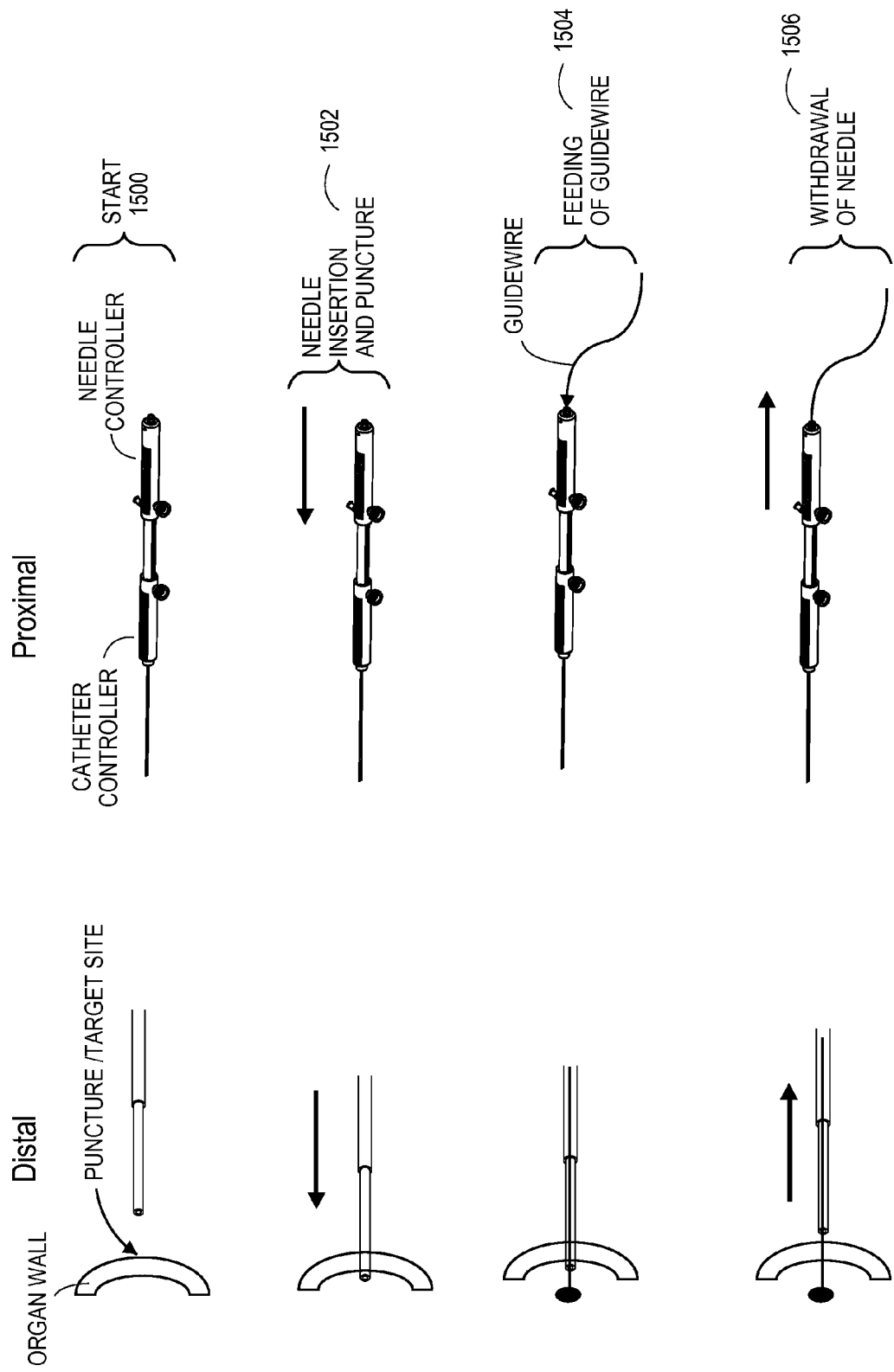
FIG. 15 illustrates the operation of an embodiment of the present invention.
Figure 15:
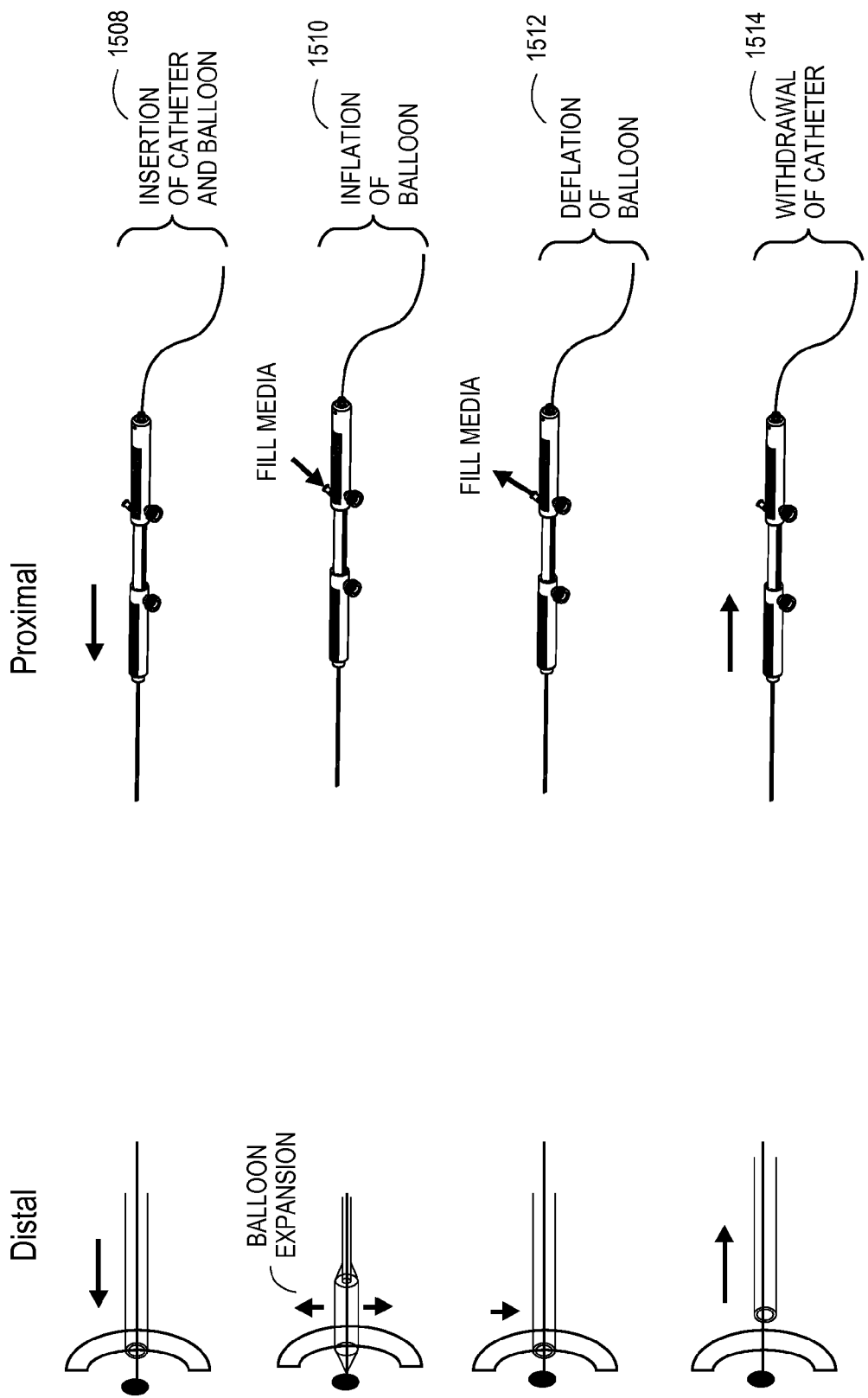

FIG. 15 illustrates the operation of an embodiment of the present invention. In stage 1500, the user has selected a desired site and has begun placing the needle via the endoscope 102 through working channel 104. The operation of accessory 106 may now be explained with reference to stages 1502 through 1514. As can be recognized, the embodiments allow the procedure to be performed with a single accessory and without the need of removing or exchanging any accessories, if desired. For purposes, of illustration, FIG. 15 shows the procedure at both the distal and proximal end.

In stage 1502, the user inserts the needle into the puncture site by selectively moving needle controller 900 forward. As noted, the user may rely upon ruler 1100 as a guide to determine how far to insert the needle.

In stage 1504, the user may feed a guidewire 108 through entry port 908. The guidewire 108 will travel through the inner lumen of needle catheter 504. At the site at the distal end, the user may then manipulate the guidewire 108 to secure it, for example, to the cyst.

In stage 1506, the user may then withdraw the needle by pulling back on the needle controller 900. Alternatively, the user may simply pull on accessory 106 to withdraw the needle.

In stage 1508, the user may then insert the balloon catheter 502 by sliding the catheter controller 800 forward. Again, the user may utilize ruler 1200 as an aid to quantitatively determine how far to insert the balloon catheter.

In stage 1510, the user then injects a fill media, for example, using an Alliance II water gun at port 904 to inflate the balloon 310. As shown, the balloon 310 inflates and dilates the puncture site at the distal end.

In stage 1512, the user then withdraws or drains the fill media from the balloon 310 out from port 904. At the distal end, the balloon 310 deflates.

In stage 1514, the user may then withdraw the balloon catheter 502 by either pulling on controller 800 or pulling accessory 106 at the proximal end. Optionally, the user may then insert other devices, such as stents, to maintain the dilated puncture site.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An endoscopic system comprising:
a multi-lumen catheter having a proximal and distal end, wherein the catheter comprises an inflatable balloon affixed to the distal end of the catheter in fluid communication with a first lumen, and a hollow needle housed within the multi-lumen catheter for independent movement relative to the inflatable balloon;
a controller that is attachable to the multi-lumen catheter and configured with a first portion, coupled to the catheter, to advance the catheter distally for placing the inflatable balloon at the desired site and a second portion, coupled to the hollow needle, to advance the hollow needle; and
a port for a guidewire, wherein the port is configured to allow the guidewire to travel within the hollow needle, wherein the hollow needle and the guidewire are configured to be extended and retracted independently of each other at a desired site within a patient.

2. The system of claim 1, wherein the controller further comprises an inner cylinder and wherein the first portion comprises a first slidable portion over the inner cylinder and a second portion comprises a second slidable portion over the inner cylinder and adapted for independent movement relative to each other.

3. The system of claim 2, wherein the endoscopic system comprises a connection that is connectable to a working channel of an endoscope.

4. The system of claim 2, wherein the first portion of the controller is connectable to the proximate end of the multi-lumen catheter.

5. The system of claim 2, wherein longitudinal movement of the first portion of the controller with respect to the inner cylinder causes advancement or retraction of the multi-lumen catheter within the working channel of the endoscope.

6. The system of claim 2, wherein the inner cylinder of the controller comprises a set of markings indicating a distance of advancement or retraction of the first portion and the second portion.

7. The system of claim 2, wherein the controller comprises a separator valve that selectably connects lumens of the multi-lumen catheter to a separate controller.

8. The system of claim 2, wherein the controller comprises a second port that is in fluid communication with the balloon.

9. The system of claim 1, wherein the hollow needle ranges from about a 19 gauge to a 23 gauge.

10. The system of claim 1, wherein the hollow needle is configured to extend about 8 cm from the distal end.

11. The system of claim 1, wherein the port is configured to accommodate a guidewire having a diameter of approximately 0.035 inches.

12. The system of claim 1, wherein the inflatable balloon is radio-opaque.

13. The system of claim 1, wherein the inflatable balloon is molded.

* * * * *